(12) United States Patent
Thomas

(10) Patent No.: US 7,152,599 B2
(45) Date of Patent: Dec. 26, 2006

(54) NASAL MASK FOR DELIVERING GAS

(76) Inventor: Wendell A. Thomas, 547 Judson Ave., Evanston, IL (US) 60202

( * ) Notice: Subject to any disclaimer, the term of this patent is extended or adjusted under 35 U.S.C. 154(b) by 6 days.

(21) Appl. No.: 11/133,774

(22) Filed: May 20, 2005

(65) Prior Publication Data

US 2006/0260615 A1    Nov. 23, 2006

(51) Int. Cl.
*A62B 18/02* (2006.01)
*A62B 18/08* (2006.01)

(52) U.S. Cl. .................... 128/205.25; 128/206.23; 128/207.13

(58) Field of Classification Search .......... 128/206.21, 128/206.24, 206.26, 206.27, 207.11, 207.13, 128/205.25, 202.28, 201.23, 201.29, 206.22, 128/206.12, 206.28, 207.21
See application file for complete search history.

(56) References Cited

U.S. PATENT DOCUMENTS

| | | | | |
|---|---|---|---|---|
| 4,799,477 A * | 1/1989 | Lewis | .................... | 128/206.24 |
| 4,971,051 A * | 11/1990 | Toffolon | ................ | 128/206.26 |
| 5,074,297 A * | 12/1991 | Venegas | ................ | 128/204.18 |
| 5,121,745 A * | 6/1992 | Israel | .................... | 128/202.28 |
| 5,535,736 A * | 7/1996 | Jzaw | .................... | 128/202.26 |
| 6,412,488 B1 * | 7/2002 | Barnett et al. | ......... | 128/207.13 |
| 6,467,483 B1 * | 10/2002 | Kopacko et al. | ....... | 128/207.12 |
| 6,532,961 B1 * | 3/2003 | Kwok et al. | ........... | 128/206.21 |
| 6,651,661 B1 * | 11/2003 | Matioc | .................... | 128/205.25 |
| 6,698,427 B1 * | 3/2004 | Clowers | ................ | 128/206.21 |
| 6,736,139 B1 * | 5/2004 | Wix | ...................... | 128/206.21 |

* cited by examiner

*Primary Examiner*—Henry Bennett
*Assistant Examiner*—Amadeus Lopez
(74) *Attorney, Agent, or Firm*—Cardinal Law Group

(57) ABSTRACT

A nasal mask for delivering gas to a mammalian nasal passage includes a body portion including an inlet opening and an outlet opening as well as a facial contact portion having an opening in communication with the outlet opening and a shroud positioned over the facial contact portion opening, wherein the shroud expands to contact the face of a user when gas is delivered through the inlet opening. A method for delivering gas includes identifying a user having a mammalian nasal passage to wear a nasal mask, and preparing a facial contact portion. The facial contact portion is placed on the user's face to contour a facial contact surface to the user's face and the facial contact portion is set. The facial contact portion is attached to a gas delivery system; and gas is delivered to the mammalian nasal passage through the gas delivery system via the facial contact portion.

15 Claims, 6 Drawing Sheets

600

700

NASAL MASK FOR DELIVERING GAS

FIELD OF THE INVENTION

This invention relates generally to a nasal mask. More specifically, the invention relates to a nasal mask for delivering a gas.

BACKGROUND OF THE INVENTION

Medical professionals often desire to treat medical conditions by delivering a gas to a patient for an extended period of time. Often a nasal mask is utilized, such that a mask is placed over a patients nose so that the gas is delivered into the vicinity of the nasal passages. Other devices deliver gas directly into the nasal passage, but such devices may be disadvantageous. However, over an extended period of wear, the devices may be uncomfortable for a user—a factor that encourages noncompliance.

The delivered gas may be therapeutic, anesthetic, atmospheric, or a controlled environment gas, such as oxygen.

Therefore, it would be desirable to provide a method and system that overcomes the aforementioned and other disadvantages.

SUMMARY OF THE INVENTION

One aspect of the invention provides a nasal mask for delivering gas to a mammalian nasal passage. The mask includes a body portion including an inlet opening and an outlet opening as well as a facial contact portion having an opening in communication with the outlet opening and a shroud positioned over the facial contact portion opening, wherein the shroud expands to contact the face of a user when gas is delivered through the inlet opening.

Another aspect of the invention provides a method for delivering gas. The method includes identifying a user having a mammalian nasal passage to wear a nasal mask, and preparing a facial contact portion. The facial contact portion is placed on the user's face to contour a facial contact surface to the user's face and the facial contact portion is set. The facial contact portion is attached to a gas delivery system; and gas is delivered to the mammalian nasal passage through the gas delivery system via the facial contact portion.

Another aspect of the invention provides a system for delivering gas to a mammalian nasal passage including a body portion including means for an inlet opening and means for an outlet opening as well as means for a facial contact portion having an opening in communication with the outlet opening and a shroud positioned over the facial contact portion opening, wherein the shroud expands to contact the face of a user when gas is delivered through the inlet opening.

The aforementioned, and other features and advantages of the invention will become further apparent from the following detailed description of the presently preferred embodiments, read in conjunction with the accompanying drawings. The detailed description and drawings, which are not to scale, are merely illustrative of the invention rather than limiting, the scope of the invention being defined by the appended claims and equivalents thereof.

DETAILED DESCRIPTION OF THE DRAWINGS

Figure 1:
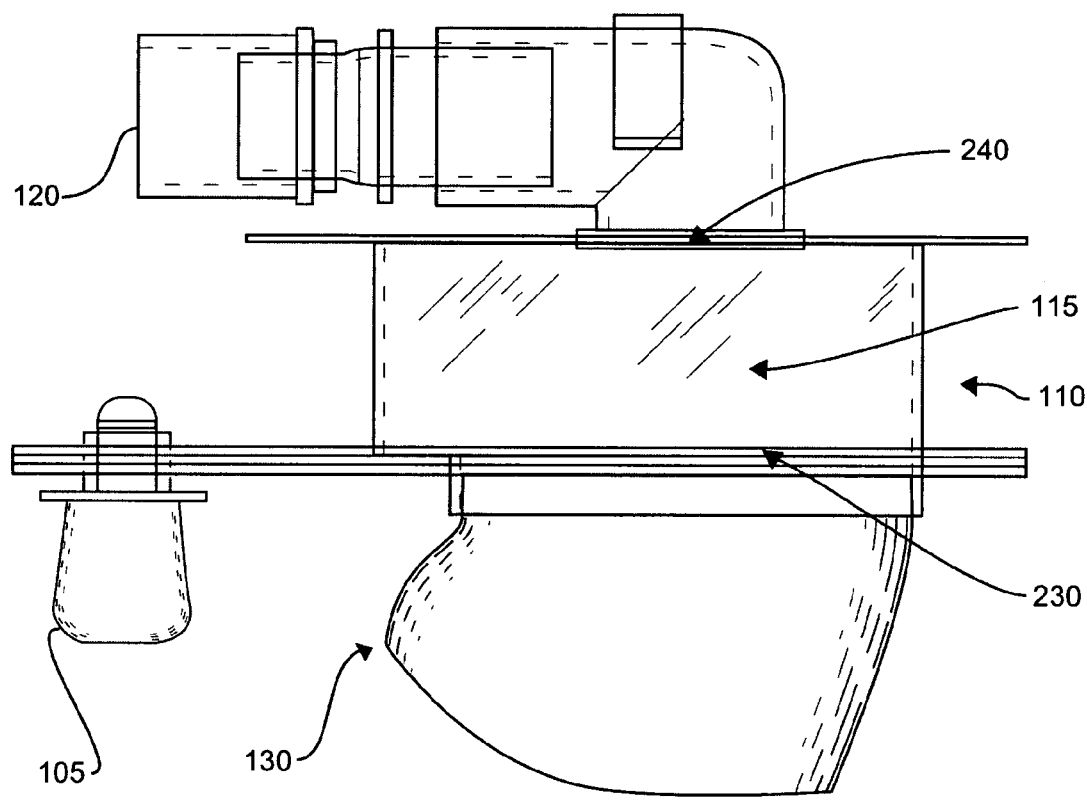
FIG. 1 is a side view of one embodiment of a nasal mask, in accordance with one aspect of the present invention.
Figure 2:
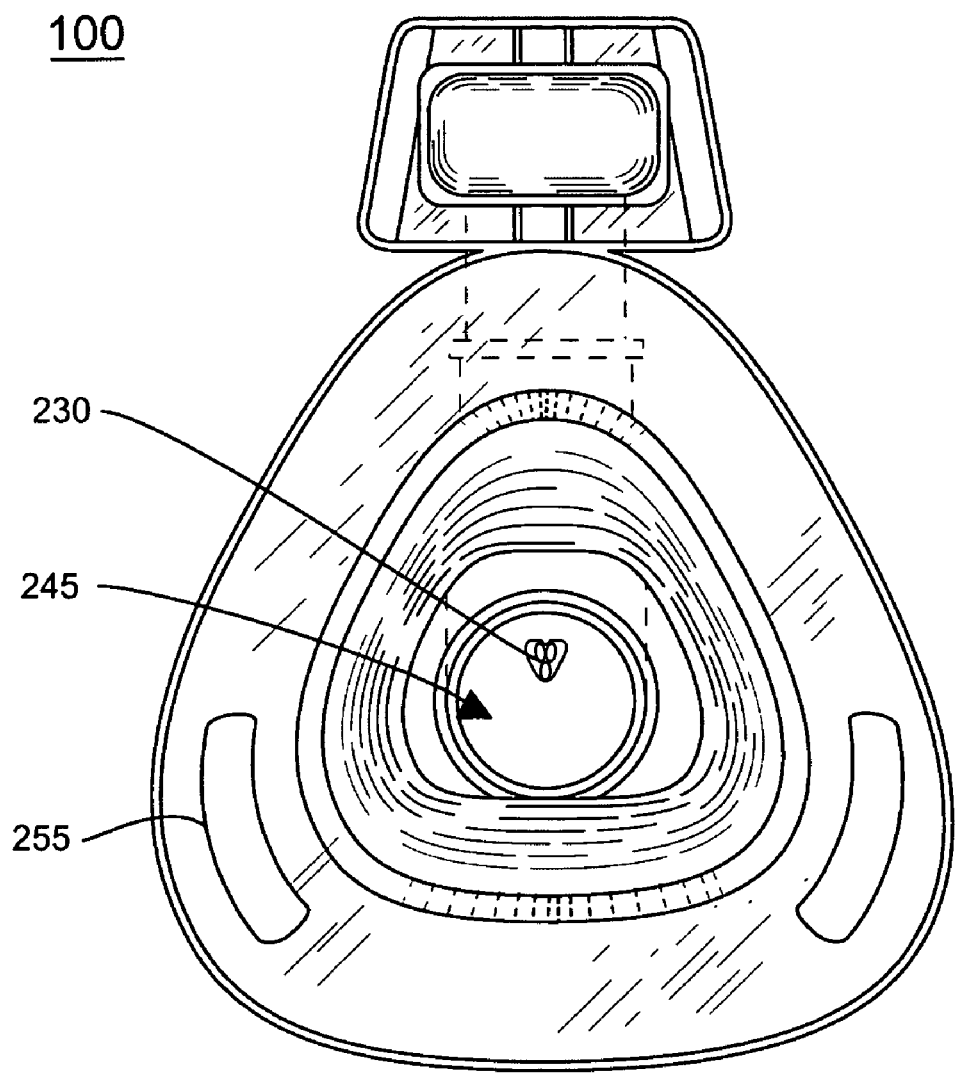
FIG. 2 is a front view of one embodiment of a nasal mask, in accordance with one aspect of the present invention.

FIG. 1 illustrates a side view, and FIG. 2 illustrates a front view, of a nasal mask 100 in accordance with one aspect of the invention. Nasal mask 100 includes body portion 110, gas inlet tube 120, which constitutes a main inlet opening, and facial contact portion 130. In one embodiment, body portion 110 includes a padded forehead portion 105 configured to rest upon a forehead of a user. The padded forehead portion 105 may comprise any appropriate padding material, such as a gel or foam.

Gas inlet tube 120 includes a lumen configured for connection to a source of gas. Body portion 110 includes a central passageway 115 in fluidic communication with the gas inlet tube 120 lumen via inlet opening 240 and an outlet opening 230. Outlet opening 230 is in fluidic communication with a facial contact portion opening 245 formed in facial contact portion 130. Body portion 110 and gas inlet tube 120 may be formed from any appropriate material, such as a plastic or other relatively rigid material. In one embodiment, body portion 110 and gas inlet tube 120 are formed from a lightweight material that maintains rigidity. In one embodiment, gas inlet tube 120 is connected to body portion 110 using a rotatable connection configured to allow gas inlet tube 120 to rotate completely around body portion 110.

Facial contact portion 130 is formed from a pliable material configured to maintain its shape. In one embodiment, facial contact portion 130 is molded. In another embodiment, facial contact portion 130 is custom molded to a user's face. In one embodiment, facial contact portion 130 comprises a moldable material that requires application of heat to configure the material into a desired shape. In another embodiment, facial contact portion 130 comprises a moldable material that requires the material to set for a period of time to configure the material into a desired shape.

Strap holes 255 are formed in body portion 110. In one embodiment, strap holes 255 are configured to accept a strap used to position nasal mask 100 on a user's face. Any number of strap holes may be utilized, although FIG. 2 illustrates 2 holes.

Figure 3:
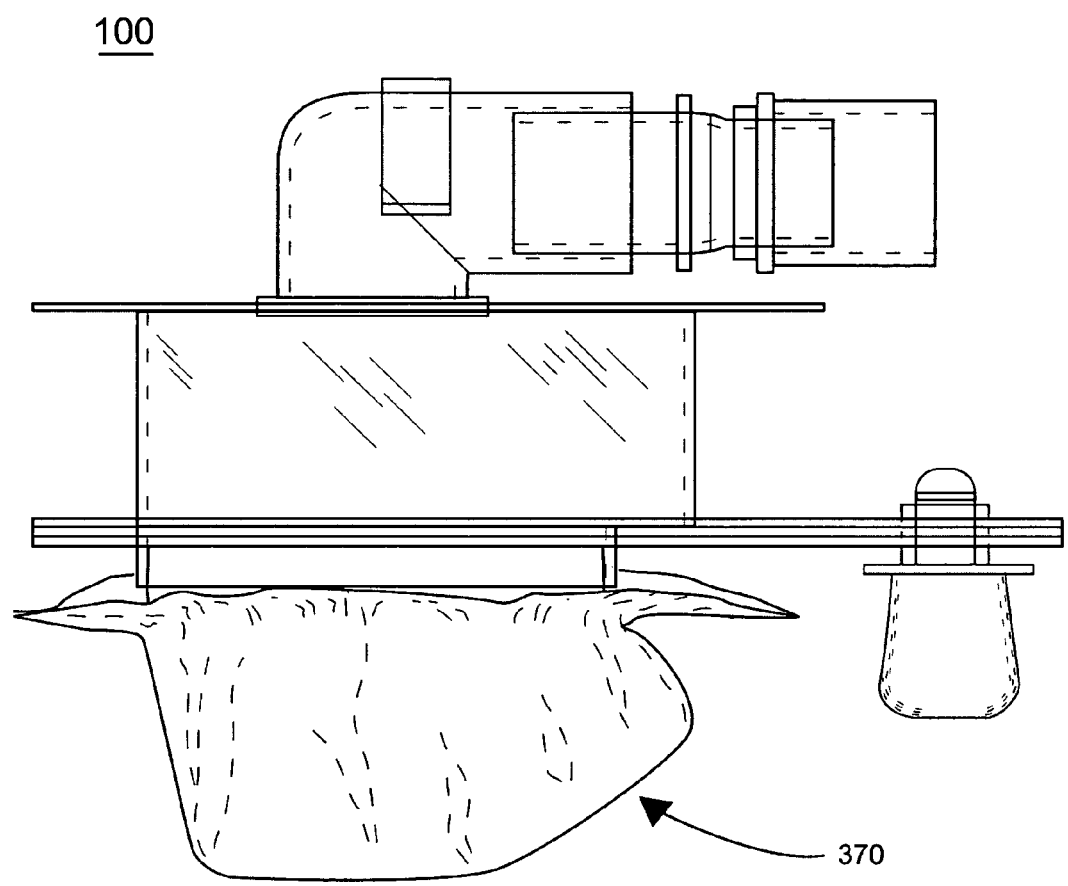
FIG. 3 is a side view of one embodiment of a nasal mask including a shroud in accordance with one aspect of the invention.

FIG. 3 illustrates nasal mask 100 with a shroud 370 positioned over the facial contact portion opening. Shroud 370 comprises any flexible material configured to change shape in response to airflow through the facial contact portion opening. When gas flows through the facial contact portion opening 245, the shroud expands as needed to contact the face of a user. In one embodiment, shroud 370 comprises a flexible plastic. In another embodiment, shroud 370 comprises a textile, such as cotton. In another embodiment, shroud 370 comprises nylon, rayon, silk, or other such material. In another embodiment, shroud 370 comprises an elastomer. In yet another embodiment, shroud 370 is formed as a flange on a surface of facial contact portion 130.

Figure 4:
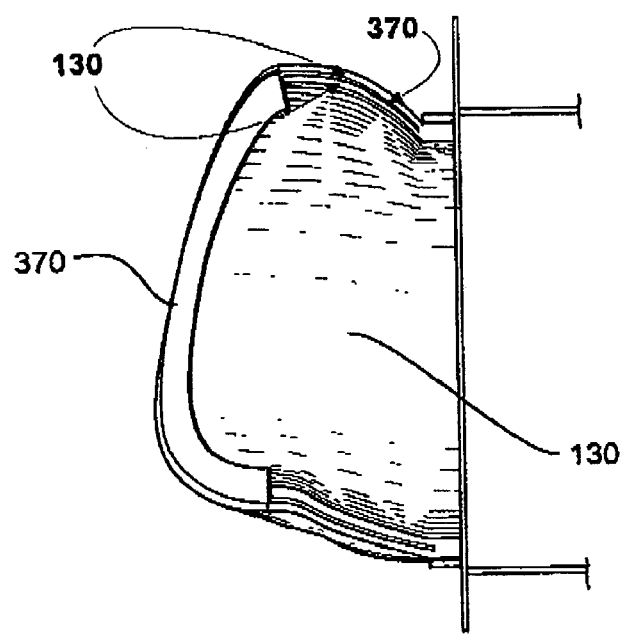
FIGS. 4 and 5 are cross sectional views of one embodiment of a facial contact portion including a shroud, in accordance with one aspect of the invention.
Figure 5:
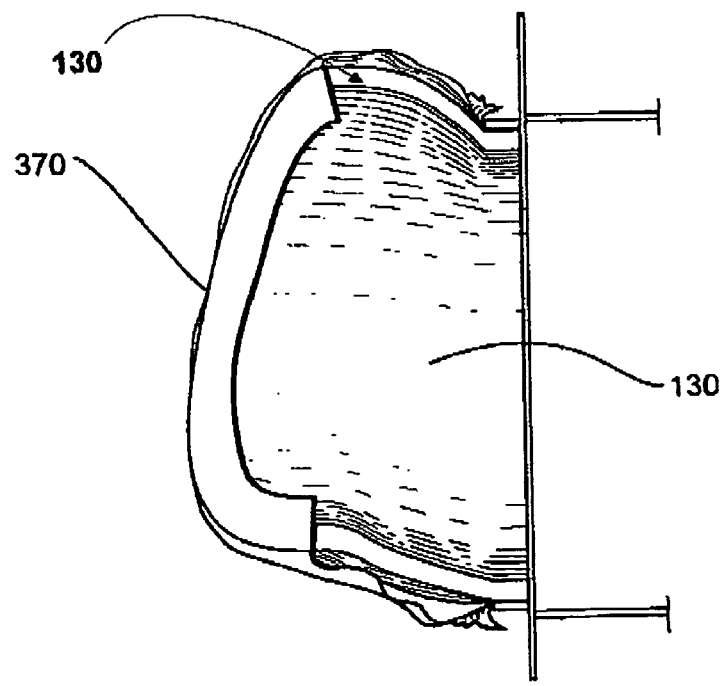

In one embodiment, illustrated in FIG. 4, shroud 370 is molded into the facial contact portion at a side where the facial contact portion connects to body portion 110. As shown in FIG. 4, facial contact portion is shown in cross section, with shroud 370 formed within, and extending from, facial contact portion 130. Conversely, FIG. 5 illustrates another cross section but shroud 370 is not molded into the facial contact portion, but is instead configured to be held in position by clamping the facial contact portion 130 to the body portion 110. Clamping the facial contact portion 130 to the body portion 110 is defined as any removable attachment technique, such as a snap fit, hook-and-loop fastener, zipper, or the like. In the embodiment illustrated in FIG. 5, the shroud is disposable.

When gas inlet tube is connected to a source (not shown) of pressurized gas, gas flows through the lumen of gas inlet tube through central passageway 115 and through the facial contact portion and the facial contact portion opening. As the gas flows through the facial contact portion opening, the gas causes the shroud to billow as needed. As the shroud billows, the shroud assumes the shape of a surface on the side opposite the gas, such as a user's face. The billowing shroud reduces impact of the facial contact portion on the user's face. In one embodiment, the facial contact portion essentially floats on a bed of gas.

Figure 6:
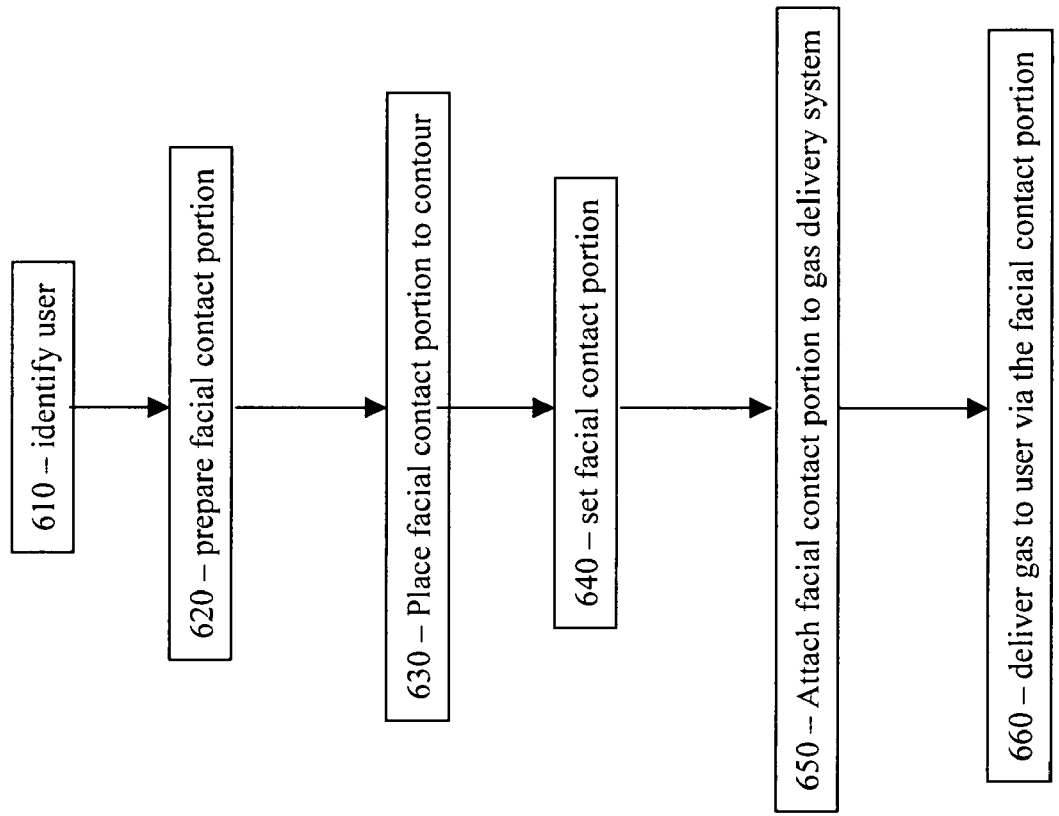
FIG. 6 illustrates one embodiment of a method for delivering gas to a mammalian nasal passage in accordance with one aspect of the invention.

FIG. 6 illustrates one embodiment of a method 600 for delivering gas to a mammalian nasal passage in accordance with one aspect of the invention. Method 600 begins at step 610 by identifying a user having a mammalian nasal passage to wear a nasal mask. For example, a human suffering from sleep apnea may be selected or prescribed to wear a nasal mask in order to treat the symptoms of sleep apnea.

A facial contact portion is prepared at step 620. The facial contact portion, in one embodiment, is implemented as facial contact portion 130 described above. In one embodiment, preparing the facial contact portion comprises filling a mold with a moldable material to be custom fit to the user's face. This molded material may or may not be used as a mold to create a facial contact portion of a different material.

The prepared facial contact portion is placed on the user's face to contour a facial contact surface to the user's face at step 630. In one embodiment, step 630 molds the facial contact portion to the user's face.

The contoured facial contact portion including the contoured facial contact surface is set at step 640. Setting the facial contact portion includes any appropriate method to set the molded material, such as heat, cold, time, or application of an enzyme or starter, or another chemical. In another embodiment, setting includes curing.

The set facial contact portion is attached to a gas delivery system at step 650. In one embodiment, the gas delivery system is implemented as the nasal mask for delivering gas to a mammalian nasal passage described in FIGS. 1–3.

After the facial contact portion is attached to the gas delivery system, gas is delivered to the mammalian nasal passage through the gas delivery system via the facial contact portion at step 660. In one embodiment, the delivered gas furls a facial contact portion of the shroud such that the contoured facial contact surface rests upon a bed of gas.

Figure 7:
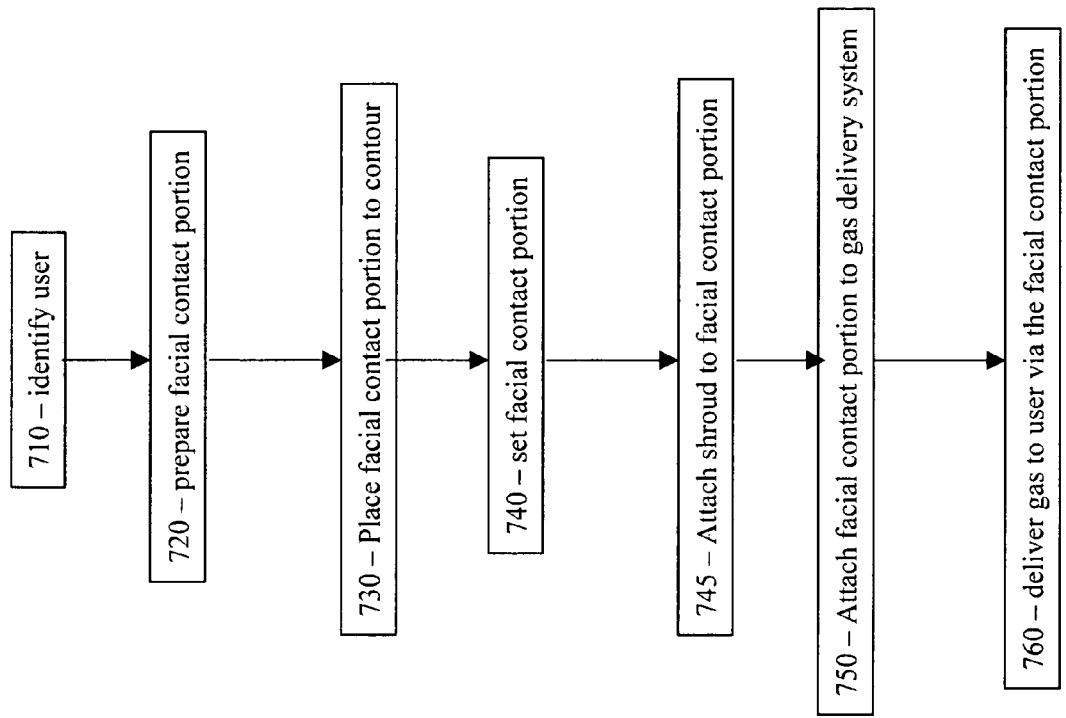
FIG. 7 illustrates another embodiment of a method for delivering gas to a mammalian nasal passage in accordance with one aspect of the invention.

FIG. 7 illustrates one embodiment of a method 700 for delivering gas to a mammalian nasal passage in accordance with one aspect of the invention. Method 700 begins at step 710 by identifying a user having a mammalian nasal passage to wear a nasal mask. For example, a human suffering from sleep apnea may be selected or prescribed to wear a nasal mask in order to treat the symptoms of sleep apnea.

A facial contact portion is prepared at step 720. The facial contact portion, in one embodiment, is implemented as facial contact portion 130 described above. In one embodiment, preparing the facial contact portion comprises filling a mold with a moldable material to be custom fit to the user's face.

The prepared facial contact portion is placed on the user's face to contour a facial contact surface to the user's face at step 730. In one embodiment, step 730 molds the facial contact portion to the user's face. This molded material may or may not be used as a mold to create a facial contact portion of a different material.

The contoured facial contact portion including the contoured facial contact surface is set at step 740. Setting the facial contact portion includes any appropriate method to set the molded material, such as heat, cold, time, or application of an enzyme or starter, or another chemical. In another embodiment, setting includes curing.

A shroud is attached to the facial contact portion at step 745. The attaching may occur during the setting process (i.e. during step 740), during the preparation process (i.e. step 720), or after setting but prior to step 750. The shroud is configured to expand as needed to contact the face of a user when gas is delivered through the facial contact portion. In one embodiment, the shroud is molded into the facial contact portion. In another embodiment, the shroud is removably attached to the facial contact portion. In yet another embodiment, the shroud is held in position between the facial contact portion and a body portion, such as body portion 110.

The set facial contact portion is attached to a gas delivery system at step 750. In one embodiment, the gas delivery system is implemented as the nasal mask for delivering gas to a mammalian nasal passage described in FIGS. 1–3.

After the facial contact portion is attached to the gas delivery system, gas is delivered to the mammalian nasal passage through the gas delivery system via the facial contact portion at step 760.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A nasal mask for delivering a gas to a mammalian nasal passage, the mask comprising:
   a body portion including a main inlet opening and an outlet opening;
   a facial contact portion having an opening in communication with the outlet opening;
   a shroud positioned over the facial contact portion opening, wherein the shroud expands to contact the face of a user when gas is delivered to a mammalian nasal passage through the main inlet opening.

2. The mask of claim 1 wherein the body portion includes strap holes.

3. The mask of claim 1 wherein the body portion further includes a padded forehead portion to rest upon a forehead.

4. The mask of claim 1 wherein the facial contact portion is formed by molding.

5. The mask of claim 1 wherein at least one edge of the shroud is molded into the facial contact portion.

6. The mask of claim 1 wherein the shroud is positioned between the facial contact portion and the body portion, the facial contact portion and the body portion holding the shroud in position.

7. The mask of claim 1 wherein the shroud is disposable.

8. The mask of claim 1 wherein the shroud is formed as a flange on a surface of the facial contact portion.

9. The mask of claim 1 wherein the facial contact portion is held in position by clamping the facial contact portion to the body portion.

10. A method for delivering gas to a mammalian nasal passage, the method including;
   identifying a user having a mammalian nasal passage to wear a nasal mask,
   preparing a facial contact portion;
   placing the facial contact portion on the user's face to contour a facial contact surface to the user's face;
   setting the facial contact portion including the contoured facial contact surface;
   attaching the facial contact portion to a gas delivery system; and
   delivering gas to the mammalian nasal passage through the gas delivery system via the facial contact portion wherein the delivered gas furls a facial contact portion of the shroud such that the contoured facial contact surface rests upon a bed of gas.

11. The method of claim 10 further comprising:
   attaching a shroud to the facial contact portion, wherein the shroud is configured to expand to contact the face of a user when gas is delivered through the facial contact portion.

12. The method of claim 10 wherein setting the facial contact portion comprises a technique selected from the group consisting of curing and heat treating.

13. The method of claim 10 wherein preparing the facial contact portion comprises filling a mold with a moldable material to be custom fit to the user's face.

14. The method of claim 11 wherein the shroud is formed as a flange on a surface of the facial contact portion.

15. A system for delivering gas to a mammalian nasal passage, the system including;
   means for identifying a user having a mammalian nasal passage to wear a nasal mask,
   means for preparing a facial contact portion;
   means for placing the facial contact portion on the user's face to contour a facial contact surface to the user's face;
   means for setting the facial contact portion including the contoured facial contact surface;
   means for attaching the facial contact portion to a gas delivery system; and
   means for delivering gas to the mammalian nasal passage through the gas delivery system via the facial contact portion wherein the delivered gas furls a facial contact portion of the shroud such that the contoured facial contact surface rests upon a bed of gas.

* * * * *